(12) United States Patent
Levy

(10) Patent No.: US 8,328,841 B2
(45) Date of Patent: Dec. 11, 2012

(54) EMBOLIZATION COIL DELIVERY SYSTEMS AND METHODS

(75) Inventor: Michael J. Levy, Rochester, MN (US)

(73) Assignee: Cook Medical Technologies LLC, Bloomington, IN (US)

( * ) Notice: Subject to any disclaimer, the term of this patent is extended or adjusted under 35 U.S.C. 154(b) by 337 days.

(21) Appl. No.: 12/154,331

(22) Filed: May 22, 2008

(65) Prior Publication Data

US 2009/0054905 A1 Feb. 26, 2009

Related U.S. Application Data

(60) Provisional application No. 60/931,312, filed on May 22, 2007.

(51) Int. Cl.
*A61M 29/00* (2006.01)
(52) U.S. Cl. ........ 606/200; 606/198; 606/194; 606/159; 623/1.11
(58) Field of Classification Search .................. 606/200, 606/191, 198, 194, 108, 159; 623/1.11
See application file for complete search history.

(56) References Cited

U.S. PATENT DOCUMENTS

| 5,108,407 | A |   | 4/1992  | Geremia et al. |
|-----------|---|---|---------|----------------|
| 5,125,395 | A | * | 6/1992  | Adair ............................ 600/121 |
| 5,304,195 | A |   | 4/1994  | Twyford, Jr. et al. |
| 5,354,295 | A | * | 10/1994 | Guglielmi et al. .............. 606/32 |
| 5,427,118 | A | * | 6/1995  | Nita et al. ...................... 600/585 |
| 5,941,888 | A | * | 8/1999  | Wallace et al. ............... 606/108 |
| 6,117,157 | A |   | 9/2000  | Tekulve |
| 6,183,491 | B1| * | 2/2001  | Lulo ............................. 606/191 |
| 6,312,421 | B1|   | 11/2001 | Boock |
| 6,458,137 | B1|   | 10/2002 | Klint |
| 6,478,773 | B1| * | 11/2002 | Gandhi et al. ................. 604/113 |
| 6,537,293 | B1| * | 3/2003  | Berryman et al. ............ 606/200 |
| 6,723,108 | B1|   | 4/2004  | Jones et al. |
| 6,835,185 | B2| * | 12/2004 | Ramzipoor et al. ............ 604/57 |
| 6,966,892 | B2| * | 11/2005 | Gandhi et al. ................. 604/114 |
| 7,014,645 | B2| * | 3/2006  | Greene et al. ................. 606/158 |
| 7,018,394 | B2| * | 3/2006  | Diaz et al. ..................... 606/200 |
| 7,344,558 | B2| * | 3/2008  | Lorenzo et al. .............. 623/1.11 |
| 2004/0158282 | A1 | | 8/2004 | Jones et al. |
| 2007/0083226 | A1 | | 4/2007 | Buiser et al. |

FOREIGN PATENT DOCUMENTS

| EP | 0882428 | 12/1998 |
| EP | 1188414 | 3/2002 |
| WO | WO 9311719 | 6/1993 |
| WO | WO 9525480 | 9/1995 |
| WO | WO 0106950 A2 | 2/2001 |

* cited by examiner

*Primary Examiner* — Gary Jackson
*Assistant Examiner* — Katrina Stransky
(74) *Attorney, Agent, or Firm* — Brinks Hofer Gilson & Lione

(57) ABSTRACT

A system and method for ultrasonically guided endoscopic (EUS) delivery of one or more embolization coils to an internal body site. The embolization coil delivery devices are preferably ultrasonically guided to the selected internal body site after being advanced through the working channel of an endoscope with its distal end located near the selected internal body site. In one aspect, the system and method may be utilized to deploy an embolization coil into a lesion to promote thrombosis and/or prevent bleeding.

12 Claims, 7 Drawing Sheets

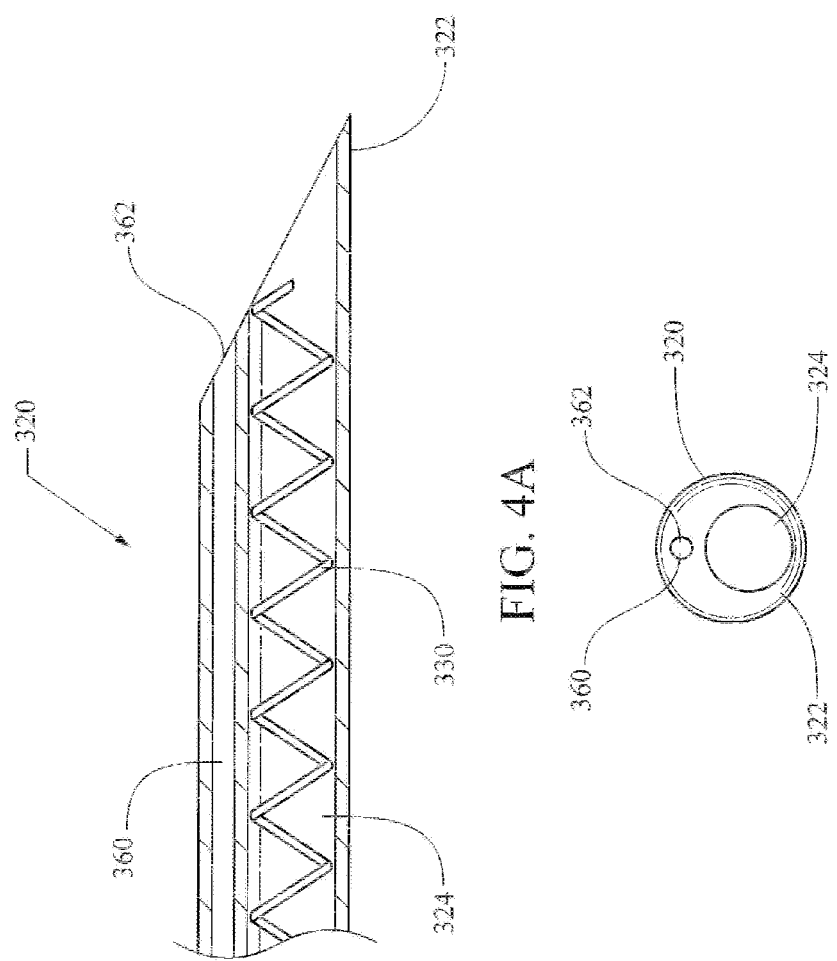

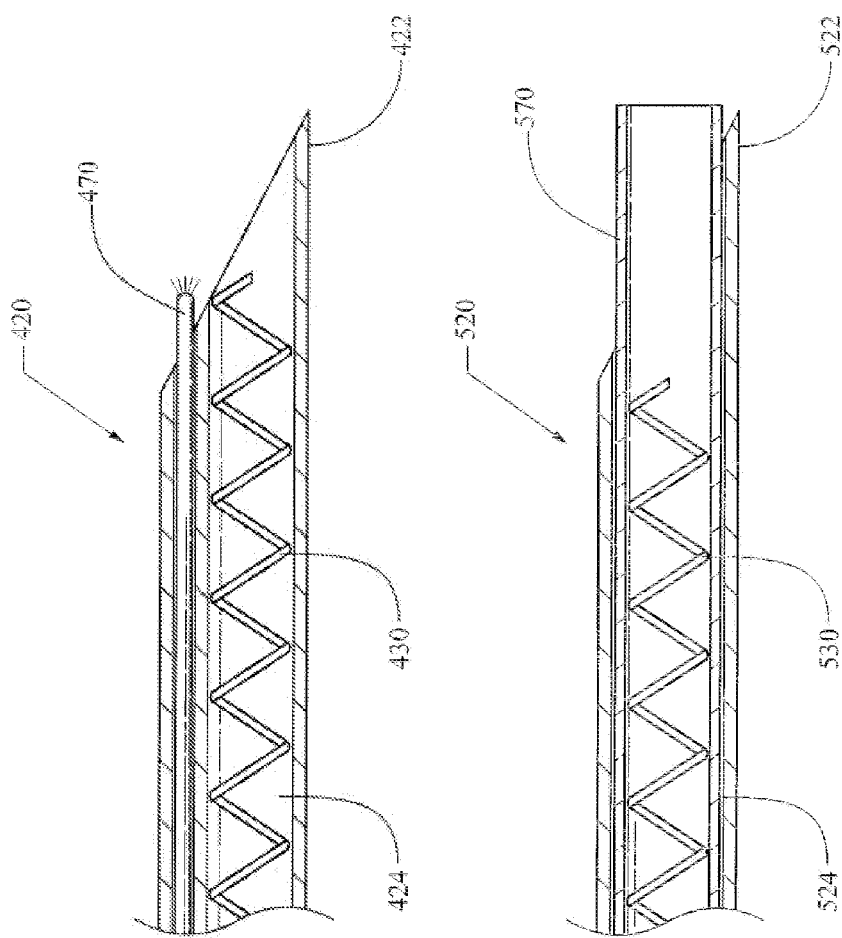

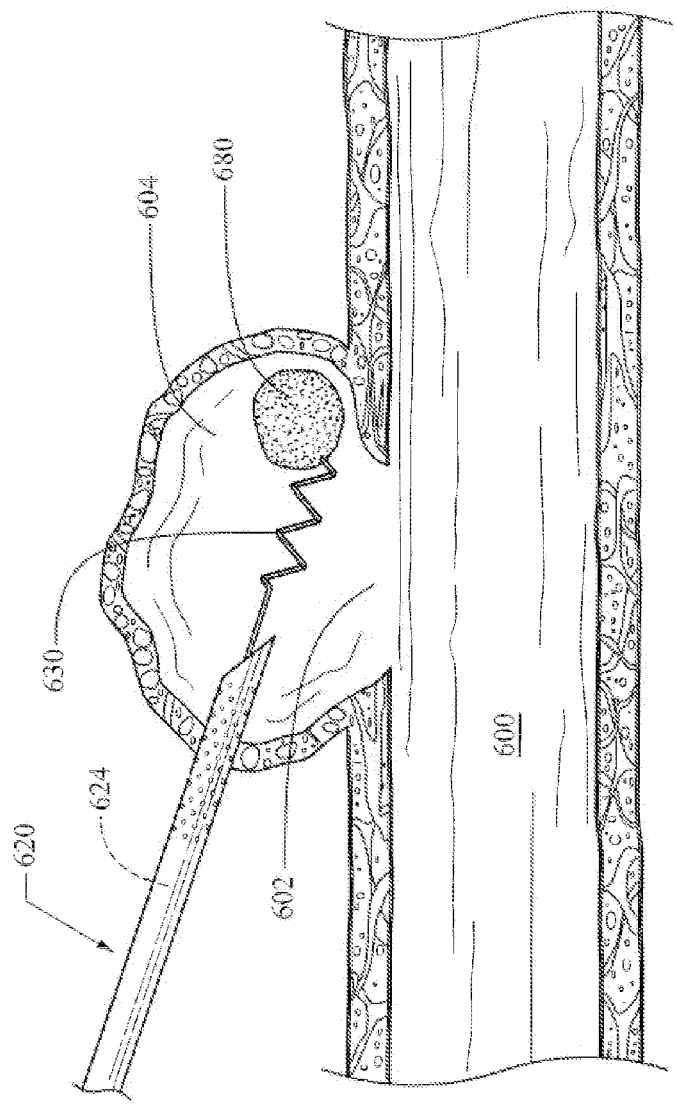

EMBOLIZATION COIL DELIVERY SYSTEMS AND METHODS

CROSS-REFERENCE TO RELATED APPLICATIONS

This application claims the benefit of U.S. Provisional Application Ser. No. 60/931,312, filed May 22, 2007, entitled "Embolization Coil delivery Systems and Methods", the entire contents of which are incorporated by reference.

TECHNICAL FIELD

The present invention relates generally to embolization coil delivery apparatus and, more particularly, to ultrasonically guided embolization coil delivery systems and methods.

BACKGROUND OF THE INVENTION

There are well-established endoscopic methods for treating internal bleeding (e.g., gastrointestinal (GI) bleeding, etc.). However, some lesions prove refractory or inaccessible to endoscopic therapy and require interventional radiological or surgical intervention.

Some examples of preloaded embolization coil delivery devices are described in U.S. Pat. Nos. 6,458,137 (Klint) and 6,117,157 (Tekulve).

BRIEF SUMMARY OF THE INVENTION

Accordingly, the present invention provides systems and methods amenable to ultrasonically guided endoscopic (EUS) delivery of one or more embolization coils to an internal body site. The embolization coil delivery devices are preferably ultrasonically guided to the selected internal body site after being advanced through the working channel of an endoscope with its distal end located near the selected internal body site.

In various aspects, the embolization coil delivery systems of the present invention include an ultrasonically detectable delivery device sized to be advanced through the working channel of an endoscope, wherein the delivery device has a lumen extending therethrough, the lumen opening at a distal end of the delivery device; one or more embolization coils located within the lumen of the delivery device; and a deployment device within the lumen of the delivery device, wherein the deployment device is adapted to eject the one or more embolization coils from the opening at the distal end of the delivery device when the delivery device is disposed through the working channel of the endoscope.

The embolization coil delivery system may include a plurality of embolization coils located within the lumen of the delivery device, such that the delivery device can be used to deliver more than one embolization coil. The plurality of embolization coils may have different sizes (in length and/or width). Alternatively, all of the embolization coils within a given delivery device lumen may be of the same size.

The plurality of embolization coils may include a visualization indicator may be located between each adjacent pair of embolization coils, which may preferably be visualized in vivo using ultrasound and/or fluoroscopy. By way of example, the visualization indicator may include material particularly susceptible to visualization using a selected technique (e.g., ultrasonically, fluoroscopically, etc.).

The plurality of embolization coils may be attached to each other within the lumen of the delivery device by an attachment mechanism, the attachment mechanism being configured to allow adjacent coils to separate from each other upon deployment of individual coils. The attachment mechanism may include a visualization indicator located between each adjacent pair of attached embolization coils of the two or more embolization coils in the lumen of the delivery device. The attachment mechanism may comprise an expandable material that is expandable in volume upon, e.g., contact with water or aqueous liquids, an increase in temperature, etc. The attachment mechanism may also comprise a thrombogenic material such as, e.g., collagen, fibrin, etc.

The plurality of embolization coils may be attached together at separation sites which are weakened to promote separation. For example, the separation sites may be weakened by, e.g., a "split-wire" design, a frayed wire design, or reduced cross-section.

In some embodiments, the delivery system may include a cutting implement located proximate the distal end of the lumen of the delivery device. The cutting implement is preferably capable of severing an embolization coil so as to form a plurality of coils. The cutting implement may be in the form of, e.g., an electrosurgical wire, a snare, or mechanical blades, and may be located in a lumen of the delivery device separate from the coil delivery lumen.

In some systems of the present invention, the delivery device may include a fluid delivery lumen in addition to the lumen in which the embolization coils are located. The fluid delivery lumen may be used to deliver fluids that may be helpful in combination with the embolization coils. Examples of some potentially suitable fluids may include, e.g., alcohols, adhesives (e.g., cyanoacrylate), solutions/suspensions containing selected materials (e.g., fibrin, collagen, contrast agents, etc.), and sclerosing agents.

In some systems of the present invention, the delivery device may include a fiber optic element that extends to the distal end of the delivery device. In one embodiment, the embolization coils are located within a lumen of the delivery device alongside the fiber optic element. In another embodiment, a hollow fiber optic element is disposed in the lumen of the delivery device, and the embolization coils are disposed within the hollow fiber optic element.

In some delivery systems of the present invention, at least one embolization coil comprises an anchor attached thereto. The anchor may be in the form of an expandable article and/or may comprise a material that may be visualized in vivo using ultrasound and/or fluoroscopy. The expansion may be provided by, e.g., hydration in response to contact with water and/or aqueous solutions, inflation, shape transformation (using, e.g., shape memory materials such as nickel-titanium alloys, etc.), or mechanical means (such as, e.g., an inflatable balloon). In some instances, the anchor may include thrombogenic or other materials.

In an exemplary method according to the present invention, a embolization coil delivery system is advanced through an endoscope to a target site within a patient. EUS is then used to guide the distal end of the delivery device into the target tissue. One or more embolization coils are then deployed from the delivery device and into the target tissue. In one aspect, the target tissue is lesion and the one or more embolization coils are inserted into the lesion to promote thrombosis thereof and/or inhibit bleeding thereofrom.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein "a," "an," "the," "at least one," and "one or more" are used interchangeably. Thus, for example, an embolization coil may refer to one, two, three, or more embolization coils unless otherwise explicitly limited.

The term "and/or" means one or all of the listed elements or a combination of any two or more of the listed elements.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF SEVERAL VIEWS OF THE DRAWINGS

Embodiments of the present invention will now be described by way of example with reference to the accompanying drawings, in which:

FIG. 4A illustrates an enlarged sectional view of the distal portion of another embodiment of a delivery device including a fluid lumen disposed adjacent to the embolization coil delivery lumen;

FIG. 4B is an end view of the distal end of the delivery device of FIG. 4A;

FIG. 5 illustrates an enlarged sectional view of the distal portion of another embodiment of a delivery device including a fiber optic element disposed adjacent to the embolization coil delivery lumen;

FIG. 6 illustrates an enlarged sectional view of the distal portion of another embodiment of a delivery device including a hollow optical element through which the embolization coils may be delivered;

FIG. 8 illustrates another method of using a delivery device to deliver an embolization coil having an anchor into a lesion.

DETAILED DESCRIPTION

Figure 1:
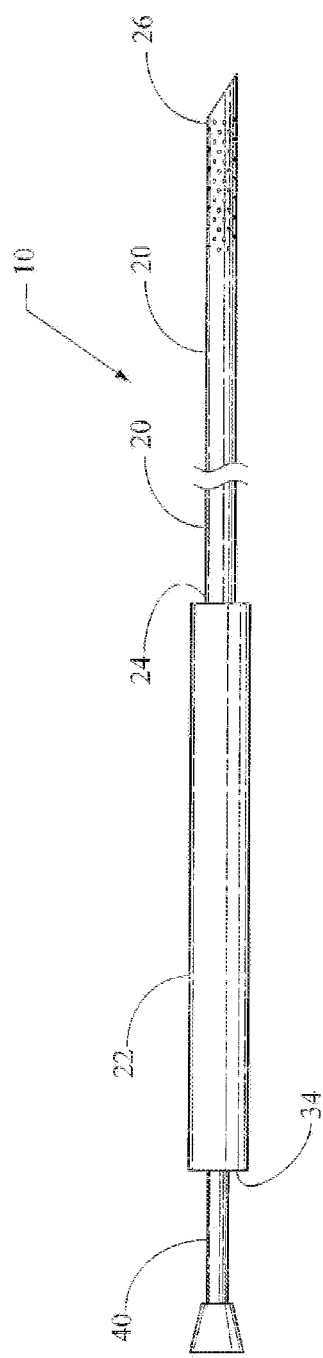
FIG. 1 illustrates an exemplary embodiment of a delivery device for delivering an embolization coil.

The invention is described with reference to the drawings in which like elements are referred to by like numerals. The relationship and functioning of the various elements of this invention are better understood by the following detailed description. However, the embodiments of this invention as described below are by way of example only, and the invention is not limited to the embodiments illustrated in the drawings. It should also be understood that the drawings are not to scale and in certain instances details have been omitted which are not necessary for an understanding of the present invention, such as conventional details of fabrication and assembly.

The present invention provides systems and methods for using endoscopic ultrasound to deliver embolization coils to internal body sites, such as the gastrointestinal tract, for the treatment of lesions or varices, and in particular the treatment of refractory ectopic variceal bleeding. In an exemplary method according to the present invention, an endoscope is inserted into a patient and positioned such that its distal end is located near the internal body site to be treated. An embolization coil delivery device is then advanced through the working channel of the endoscope until the distal end of the delivery device extends beyond the distal end of the endoscope. Endoscopic ultrasound (EUS) visualization is then utilized to guide the distal end of the delivery device to, and in some cases into, the target tissue to be treated. One or more embolization coils are then delivered to the target tissue by the delivery device. For example, one or more embolization coils may be injected into a lesion to inhibit blood flow within the lesion, i.e., to cause thrombosis in the varices. EUS visualization may be utilized to guide and monitor the delivery of the embolization coils into the target tissue.

Figure 1A:
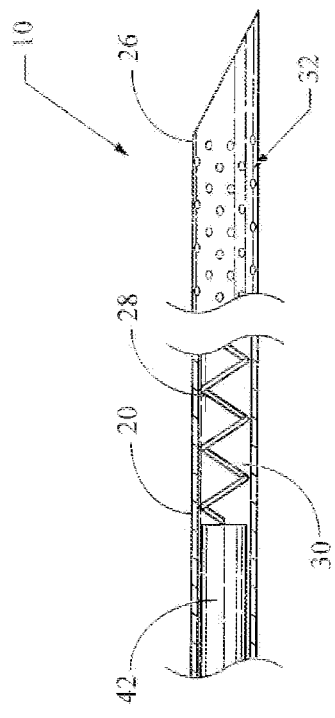
FIG. 1A is an enlarged, partially sectioned view of the distal portion of the delivery device of FIG. 1.

One embodiment of a delivery device 10 that may be utilized in the above-described method is illustrated in FIGS. 1 and 1A, wherein FIG. 1A is an enlarged, partially sectioned view of the distal portion of the delivery device 10 of FIG. 1. The delivery device 10 comprises an elongate tubular shaft 20 that is preferably sized to be advanced through the working lumen (accessory channel) of an endoscope (not shown). In some embodiments, the shaft 20 has a length sufficient to reach the biliary tree of a human patient, which is typically in the range of 120 to 140 cm. However, other lengths may be employed depending of the location of the target tissue within the patient. A handle 22 is connected to the proximal end 24 of the shaft 20 and is configured to be grasped by a user. The handle 22 may comprise ergonomic features, such as a roughened surface or indentations, to enhance the tactile feel thereof. The handle 22 may also comprise a port 34 configured for attachment to a medical syringe for the introduction of saline, contrast or other fluids therethrough. Saline is often injected into the delivery device 10 immediately prior to initiation of the medical procedure to remove air and/or provide lubrication to the device.

The distal end 26 of the shaft 20 is preferably configured to penetrate bodily tissue, i.e., is shaped in the form of a needle that is capable of penetrating tissue until the selected internal body site may be reached by the distal end 26 of the device 10. In the particular embodiment illustrated, the distal end 26 has a sharpened beveled tip, however other tip configurations may be utilized depending on the diameter of the shaft 20 and the tissue intended to be penetrated. A lumen 28 extends through the handle 22 and the shaft 20, and terminates in an opening in the distal end 26 of the shaft 20. In the embodiment illustrated, the proximal end of the lumen 28 is in fluid communication with the port 34 in the handle 22 to permit fluid to be injected through the lumen 28, e.g., to flush air from the lumen 28. As will be explained in greater detail below, the lumen 28 is configured for the passage of one or more embolization coils 30 therethrough.

The delivery device 10 may preferably be ultrasonically detectable such that its advancement and position within the patient can be guided using ultrasonic visualization equipment. In particular, the distal end 26 of the tubular shaft 20 may comprise an outer surface having enhanced ultrasonically reflectivity 32, which in the embodiment illustrated is accomplished by the addition of a pattern of indentations disposed about the outer surface of the shaft 20 that aid in maneuvering and positioning the distal end 26 under ultrasound imaging (in conjunction with or as an alternative to positioning the distal end 26 using endoscopic guidance). Additional examples of some potentially suitable materials and techniques for manufacturing ultrasonically detectable articles are described in U.S. Pat. No. 5,081,997 to Bosley, Jr., et al., entitled "Echogenic Devices, Material and Method", the entire contents of which are hereby incorporated by reference.

As mentioned above, the lumen 28 of the delivery device 10 is configured for the passage of one or more embolization coils 30 therethrough. In general, one or more embolization coils 30 are inserted into the lumen 28 and positioned near the distal end 26 of the shaft 20. The coils 30 may be loaded into the proximal end of the lumen 28 once the delivery device 10 has been inserted into the patient, or may be pre-loaded into the lumen 28 prior to initiation of the medical procedure. Pre-loading of the coils 30 into the lumen 28 is generally preferable because it reduces the time and complexity of the medical procedure. Pre-loading of the coils 30 may also limit or prevent the entry of air into the lumen 28 of the delivery device 10, which can impair EUS visualization.

Once the delivery device 10 is correctly positioned, i.e., adjacent to the target tissue, a deployment device 40 is used to push the one or more embolization coils 30 out of the distal end of lumen 28 of the delivery device 10 and into the target tissue. In the particular embodiment illustrated, the deployment device 40 comprises a stylet or push rod that is inserted into the proximal end of the lumen 28 (i.e., through the handle 22) and advanced until the distal end 42 engages the proximal end of the coil 30, as illustrated in FIG. 1A. Further advancement of the deployment device 40 forces the coil 30 out of the distal end 26 of the delivery device 10. In particular, the embolization coils 30 are ejected from the device 10 through an opening at the distal end of the lumen 28, which is preferably disposed in the distal end 26 of the device 10.

An exemplary delivery device for delivering an embolization coil that may be suitable for the method of the present invention is disclosed in U.S. Patent Publication No. 2006/0142789 to Lehman et al., entitled "Method and Apparatus for Augmentation of a Sphincter", the entire contents of which are hereby incorporated by reference. Additional examples of embolization coil delivery devices are also described in U.S. Pat. No. 6,458,137 to Klint, entitled "Assembly for Positioning an Embolization Coil in the Vascular System and a Method of Introducing a Detachable Embolization Coil", and U.S. Pat. No. 6,117,157 to Tekulve, entitled "Helical Embolization Coil", the entire contents of which are each hereby incorporated by reference.

Figure 2:
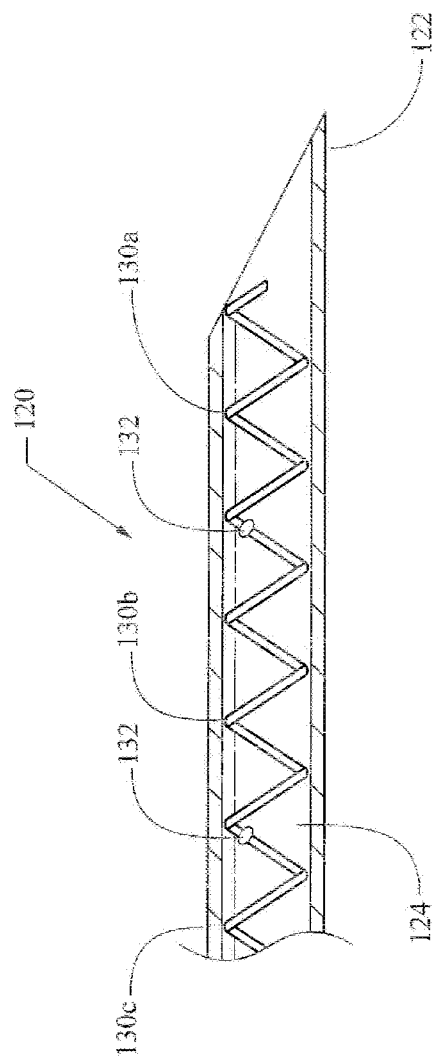
FIG. 2 illustrates an enlarged sectional view of the distal portion of another embodiment of a delivery device configured for delivering multiple embolization coils.

In some instances, lesions may be too large for a single embolization coil to occlude or cause thrombosis thereof. Thus, it may be necessary for two or more embolization coils to be deployed into the lesion. Referring to FIG. 2, the distal end of a preloaded delivery device 120 of the present invention is illustrated. The delivery device 120 comprises multiple individual embolization coils 130a, 130b, 130c, etc. (collectively referred to as embolization coils 130) that can be individually or collectively deployed based on a physician's preference and/or the size of the lesion or other target tissue. The use of a delivery device 120 that is preloaded with multiple embolization coils 130 may allow the lesion to be adequately treated without having to remove the delivery device 120 to either load an additional embolization coil into the device 120 or introduce a second delivery device, thereby reducing the duration and complexity of the medical procedure. Other aspects of the delivery device 120 are similar to the delivery device 10 shown in FIG. 1 and as described above, and will therefore not be repeated here.

In the embodiment illustrated, the delivery device 120 includes multiple embolization coils 130 of generally the same size, where the size of the coil is represented by its length as measured longitudinally along the length of the delivery device 120 and/or its width as measured across the lumen 124 transverse to the length of the coil. Alternatively, the delivery device 120 may comprise a plurality of embolization coils 130 having different sizes. For example, coils 130a, 130b, and 130c may each have a length that is progressively larger for each successive coil 130 in a proximal direction. Such a configuration would allow the shortest coil to be deployed first, and then slightly larger coils to be successively deployed thereafter, which may be advantageous when treating a lesion of undetermined size. The coils 130 are preferably be contained within the lumen 124 in a manner such that they do not slide over each other or otherwise become entangled within the lumen 124. This will also permit the pushing force to be transferred from the deployment device (see FIG. 1) and through successive coils 130c, 130b so as to permit deployment of the distal most coil 130a.

In some embodiments, the coils 130 may be attached to each other within the lumen 124. In the particular embodiment illustrated in FIG. 2, adjacent pairs of coils (e.g., coils 130a and 130b) may be attached to each other using an attachment mechanism 132. Separation of the coils 130 may preferably occur as or shortly after the attachment mechanism 132 is advanced beyond the distal end 122 of the delivery device 120. The attachment mechanism 132 may take a variety of forms, as will be described below. In some instances, the attachment mechanisms 132 may also serve as a visualization indicator that can be visualized in vivo using, e.g., ultrasound, fluoroscopy, etc.

In some embodiments, the attachment mechanism 132 may take the form of a dissolvable material (e.g., a material that dissolves or weakens when contacted with water or other aqueous fluids) such that the attachment mechanism 132 weakens to allow separation of the attached adjacent coils 130. One example of a potentially suitable dissolvable material is described in, e.g., U.S. Pat. No. 5,356,149 to Kane, entitled "Injection Molded Water—Soluble Golf Ball", the entire contents of which are hereby incorporated by reference. The dissolvable material may further include visualization agents that permit the material to be visualized using, e.g., ultrasound, fluoroscopy, etc.

In other embodiments, the adjacent embolization coils 130 may be attached to each other by a sponge material that enlarges upon contact with the environment. The sponge material may be in addition to a dissolvable material (as described above), or may comprise dissolvable portion thereof so as to permit separation of adjacent coils 130 upon deployment. The sponge could include a thrombogenic agent (e.g. collagen, fibrin, thrombin, cyanoacrylate, collagen, etc.) to promote embolization of the lesion. Examples of some potentially suitable sponge materials are described in, e.g., U.S. Pat. No. 6,548,729 to Seelich et al., entitled "Fibrin Sponge", and U.S. Patent Publication No. US 2005/0214277 to Schauffler, entitled "Suspension Comprising Fibrinogen, Thrombin and Alcohol, a Method For Preparing Such Suspension, a Method For Coating a Carrier With Such a Suspension, a Method of Drying a Coating of a Carrier, and a Coated Collagen Sponge", the entire contents of each of which are hereby incorporated by reference.

In still other embodiments, the attachment mechanism 132 may take the form of a separation site at which the embolization coil 130 is weakened or otherwise configured to promote separation. For example, adjacent embolization coils 130 may be attached to each other at separation sites 132 that comprise a weakened structure, e.g., a "split-wire" design, a frayed wire design, etc. The weakened structure may also comprise a portion of the coil 130 having a reduced cross-section or which has been partially severed. In one preferred embodiment, the attachment mechanism 132 comprises a portion of the coil 130 that has been weakened sufficiently to allow failure upon bending, wherein the bending can only be achieved once the attachment mechanism 132 has been advanced out of the lumen 124 of the delivery device 120. This will permit the separation of adjacent coils 130 from each other.

Figure 3A:
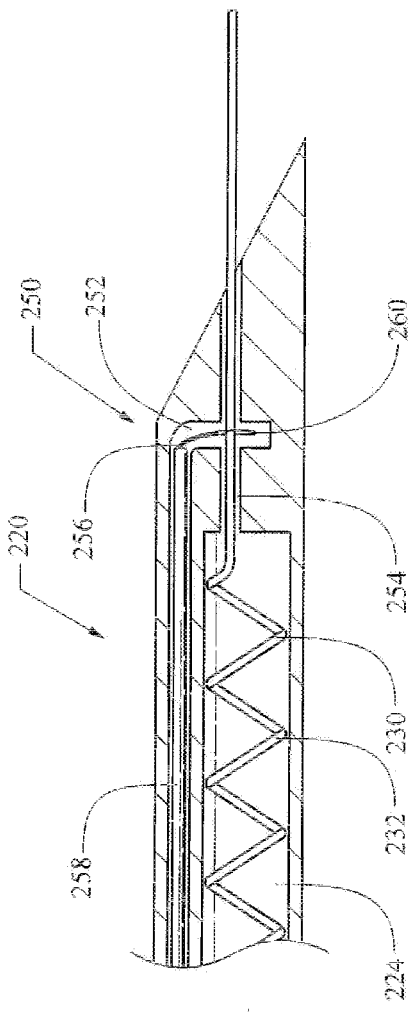
FIG. 3A illustrates an enlarged sectional view of the distal portion of another embodiment of a delivery device including a cutting implement for cutting a continuous wire into multiple individual embolization coils.
Figure 3B:
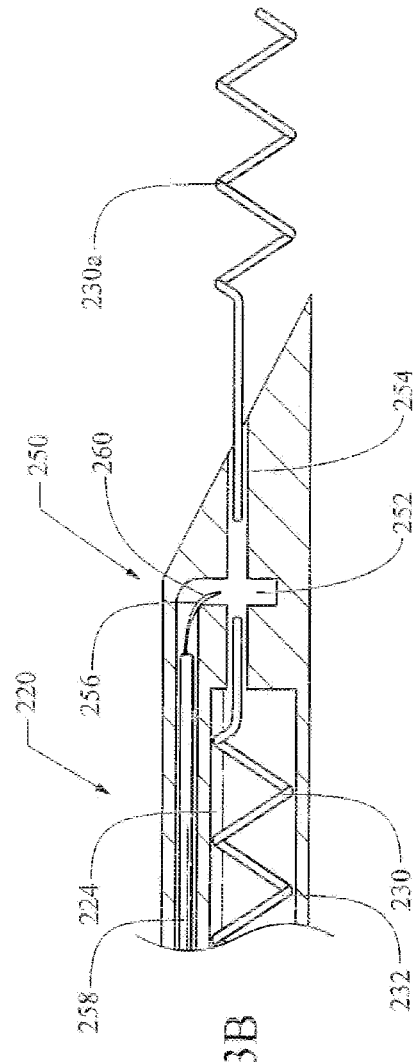
FIG. 3B is another view of the embodiment FIG. 3A after the cutting implement has been utilized to cut the continuous wire to so as to form an individual embolization coil.

FIGS. 3A and 3B illustrate another embodiment of the embolization coil delivery device 220 of the present invention that is configured to deploy one or more embolization coils 230. This embodiment is therefore similar in function to the delivery device 120 shown in FIG. 2 and described above in that the delivery device 220 is capable of deploying a plurality of individual embolization coils (collectively referred to as embolization coils 230). However, the delivery device 220 shown in FIGS. 3A and 3B utilizes a single, relatively long embolization coil 230 that may be severed to form a plurality of smaller individual coils. In particular, the delivery device 220 comprises a single relatively long embolization coil 230 that is disposed within the lumen 224 of a delivery device 220 and is formed from a continuous wire 232. A cutting implement 250 is disposed at the distal end 222 of the delivery device 220 and is configured to sever the wire 232 so as to form a separate smaller coil 230a (see FIG. 3B).

In the particular embodiment illustrated, the cutting implement 250 comprises a cutting lumen 252 that traverses and is in operable communication with a guide lumen 254, which in turn is in communication with the lumen 224 of delivery device 220. The wire 232 of the coil 230 passes through the guide lumen 254 and is temporarily straightened and supported thereby. A cutting wire 256, such as electrosurgical wire, is disposed in the cutting lumen 252 and is configured to engage and sever the portion of the wire 232 that extends through the guide lumen 254 to thereby forming a separate smaller coil 230a (see FIG. 3B).

In one exemplary embodiment, the cutting wire 256 comprises an operating wire 258 that extends through the cutting lumen 252 and is connected at its proximal end to the handle (not shown) of the delivery device 220. The handle is configured to allow a user to retract or advance the operating wire relative to the cutting lumen 252. Various types of handles for use with elongate medical devices and capable of manipulating an operating wire of the medical device are well known to those skilled in the art and will therefore not be described here. In any event, the details of construction of such known handles are not critical to present invention. A loop or snare 260 is disposed on the distal end of the operating wire 258 and, as shown in FIG. 3A, is disposed about the guide lumen 254 and the wire 232. Once the user has deployed a desired amount of the wire 232 so as to form a coil 230a of the desired size, the handle is manipulated to retract the operating wire 258. This action pulls the snare 260 across the guide lumen 254 to thereby sever the wire 232, as shown in FIG. 3B. The user may subsequently deploy an additional coil by repeating the above-described steps, i.e., by advancing and severing an additional segment of wire 232 so as to form another coil of desired size.

It should be noted that other types of cutting implements 250 and configurations thereof are contemplated. For example, the cutting implement 250 may comprise a forceps type of cutting device having a pair of rigid, hingedly connected cutting blades that may be closed to sever the wire 232 of the coil 230. In addition, the cutting implement 250 may be employed in combination with the attachment mechanism 132 of the above-describe embodiment shown in FIG. 2.

The delivery device 220 provides the ability to selectively deploy an embolization coil 230a of any size based on a physician's preference and/or the size of the lesion or other target tissue. It also eliminates the need to deploy multiple coils 230, although multiple coils may be deployed if desired, for example, if treating more than one lesion.

In addition to embolization coils, it may be advantageous to deliver one or more fluids, such as sclerosing agents, to treat a lesion. Sclerosing agents are chemical irritants that are injected into a lesion to cause thrombosis thereof, and are well know to those skilled in the art. The delivery of fluids is typically accomplished by the use of an elongate medical device specifically configured for the delivery and/or injection of the fluids into the lesion. However, the use of separate fluid delivery device often necessitates the removal of the embolization coil delivery device from the patient before the fluid delivery device may be introduced and advanced into the patient because of dimensional constraints of the introducer, endoscope or bodily lumen through which these devices are passed. As a result, the exchange of these devices may increase the duration and complexity of the medical procedure, with obvious potential negative consequences to the patient. Accordingly, a multi-lumen embolization coil delivery device 320 having a dedicated fluid delivery lumen is contemplated, and embodiment of which is illustrated in FIGS. 4A and 4B.

The delivery device 320 is configured to allow deployment of both embolization coils and one or more fluids. As shown in FIGS. 4A and 4B, the delivery device 320 includes a first lumen 324 in which one or more embolization coils 330 are disposed. The coils 330 may be deployed from the first lumen 324 in a manner similar to that described above in connection with either the delivery device 10 shown in FIG. 1 or the delivery device 120 shown in FIG. 2, although other mechanisms for deploying the embolization coils 330 may also be employed. The delivery device 320 further includes a second lumen 360 configured for fluid delivery. The second lumen 360, also referred to as a fluid delivery lumen, comprises an opening 362 at the distal end 322 of the delivery device 320 through which fluid can be delivered to the target tissue. Although shown in the distal end 322 of the delivery device 320, the opening 362 may be located elsewhere, such as through the side wall of the delivery device 320. The proximal end of the fluid delivery lumen 360 is connected to a port in or near the handle (not shown) of the delivery device 320. The port (not shown) may comprise a connector, such as a standard female (or male) luer fitting adapted for connection to a medical syringe. The delivery device 320 may comprise additional lumens for other purposes or functions.

Additional embodiments of the present invention are shown in FIGS. 5 and 6, which illustrate embolization coil delivery devices having fiber optic elements configured to provide for direct visualization of the embolization coils and/or the lesion. In the embodiment illustrated in FIG. 5, the delivery device 420 includes a lumen 424 in which one or more embolization coils 430 are disposed. The coils 430 may be deployed from the lumen 424 in a manner similar to that described above in connection with either the delivery device 10 shown in FIG. 1 or the delivery device 120 shown in FIG. 2, although other mechanisms for deploying the embolization coils 430 may also be employed. The delivery device 420 further includes a fiber optic element 470 that is preferably be positioned at the distal end 422 of the delivery device 420 to allow a practitioner to visually monitor the delivery of the embolization coils 430 to the lesion. The fiber optic element 470 may be extendable beyond the distal end 422 of the delivery device 420.

In the embodiment illustrated in FIG. 6, fiber-optic element 570 comprises hollow tube through which the embolization coils 530 may be delivered. The hollow tube of the fiber optic element 570 is preferably disposed within the lumen 524 of the delivery device 520, although other configurations are contemplated. The fiber optic element 570 may be extendable beyond the distal end 522 of the delivery device 520.

Figure 7:
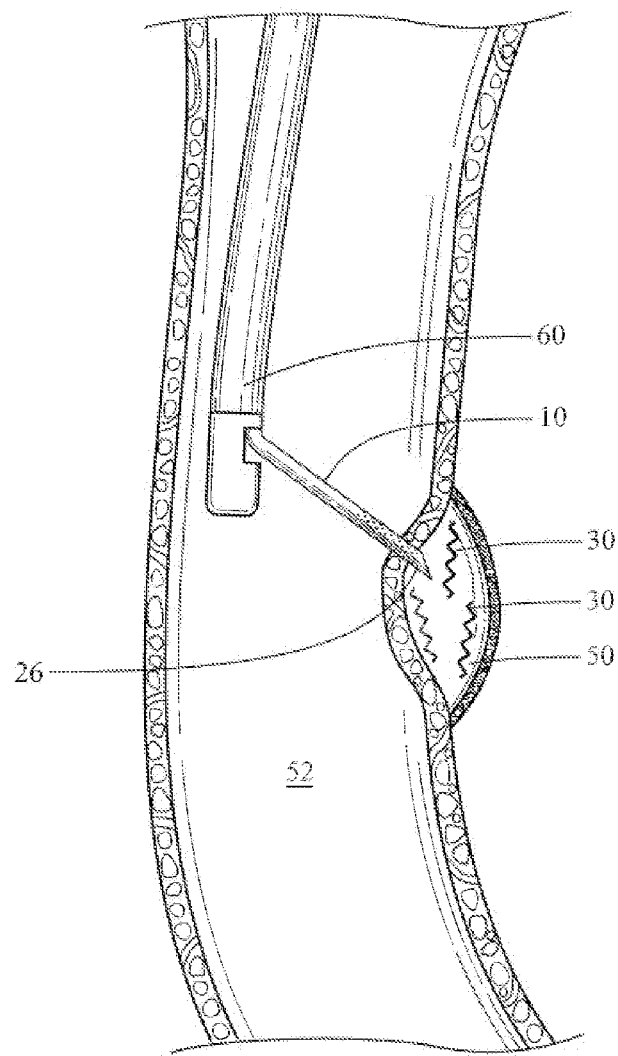
FIG. 7 illustrates an exemplary method of using a delivery device to deliver an embolization coil into a lesion.

A description of an exemplary method of using an embolization coil delivery device to treat a lesion will be described with reference to FIG. 7. In the particular method illustrated, the embodiment of the delivery device 10 shown in FIG. 1 is utilized to deliver one or more embolization coils 30 to the lesion 50. However, it should be understood that other embodiments of the delivery device, such as those described above, may be utilized. The delivery device 10 is typically advanced into the patient and towards the lesion 50 through an endoscope 60 that has been previously introduced into the gastro-intestinal tract 52 of the patient by advancing the endoscope through the patient's mouth and esophagus. The delivery device 10 is then advanced, with the aid of endoscopic ultrasound guidance, until the distal end 26 of the delivery device 10 penetrates the lesion 50. One or more embolization coils 30 are then deployed from the distal end 26 of the delivery device and into the lesion 50. Endoscopic ultrasound be employed to guide and/or assess the placement of the coils 30 within the lesion 50. Once the physician is satisfied that a sufficient number of embolization coils 30 have been properly positioned within the lesion to promote thrombosis thereof, the distal end 26 of the delivery device 10 is withdrawn from the lesion 50. The delivery device 10 may then be removed from the patient, or utilized to treat additional lesions.

FIG. 8 depicts another method of using an embolization coil delivery device 620 to deliver one or more embolization coils 630 (from a lumen 624 of the delivery device 620) to a lesion 604 that is located off of a vessel 600. As illustrated, the lesion 604 is in fluid communication with the vessel 600 through opening 602. In some instances, the opening 602 between the lesion 604 and the vessel 600 may be comparatively large. As a result, the deployed embolization coils 630 may migrate from the lesion 604, through the opening 602, and into the vessel 600. As a consequence, it may be advantageous to provide an anchor 680 attached to one or more of the embolization coils 630 to reduce the likelihood that the embolization coil 630 will migrate from the lesion 604 and enter the vessel 600. The anchor 680 may take a variety of forms. For example, the anchor 680 may be in the form of an expandable structure, such as expandable foam or a sponge of the type described above in connection with the embodiment shown in FIG. 2. Expansion of the anchor 680 may also be provided by, e.g., hydration in response to contact with water and/or aqueous solutions. The anchor 680 may also comprise a mechanically expandable structure, such as an inflatable balloon. The anchor 680 may also comprise an alloy or polymer material capable of shape transformation, such as shape memory nickel-titanium alloys. In addition, the anchor 680 may comprise a material that can be visualized in vivo using ultrasound and/or fluoroscopy, such as a radiopaque material. In some instances, the anchor 680 may include thrombogenic or other materials (e.g., contrast agents, etc.), depending on the nature or location of the lesion or tissue to be treated.

In another exemplary method, EUS was used to guide an endoscopic ultrasound needle to deploy embolization coils into several refractory ectopic (anastomotic) varices to treat variceal bleeding in a 50-year-old patient. A 22-gauge needle (Echotip® Endoscopic Ultrasound Needle, product number EUSN-3, manufactured by Cook Endoscopy, Winston-Salem, N.C.) was loaded with a microcoil (Tornado® Embolization Microcoil™, product number MWCE-185-8/4-tornado, manufactured by Cook Inc, Bloomington, Ind.). The stylet supplied with the needle was used to advance the constrained coil to the distal tip of the needle. Linear EUS (utilizing a GF-UC140P-AL5 gastrovideoscope, manufactured by Olympus America Inc., Center Valley, Pa.) was then used to guide the needle towards and into several varices within a patient (previously identified using EUS). Once the needle was inserted into a 1.4 cm varix, the stylet was further advanced to deploy the coil. The needle was subsequently used to deploy coils into two other varices. Blood flow within each of the treated varices was observed to cease after approximately 10 minutes. Minimal self-limited bleeding was observed at the puncture site during the procedure. The patient was subsequently discharged, but presented later with recurrent bleeding, although less severe, based on clinical parameters and a Hb level of 10.4 g/dL. Repeat EGD, colonoscopy, and angiography were all negative. Interventional radiological surgical staff declined intervention and favored repeat EUS therapy. At EUS, the previously treated varices were thrombosed. Two additional coils were placed into untreated varices. The patient remained free of bleeding at last follow-up, 1 month after therapy.

Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman's Medical Dictionary, 27th edition.

The invention claimed is:

1. An endoscopic embolization coil delivery system for use in treating a lesion within the gastro intestinal tract of a human patient, the delivery system comprising:

an ultrasonically detectable delivery device comprising an elongate shaft sized to be advanced through a working channel of an endoscope, the shaft having a sufficient length to reach a target tissue within the gastro intestinal tract of a patient, wherein the shaft comprises a first lumen and a second lumen extending therethrough, the first lumen comprising an opening at a distal end of the delivery device, the second lumen intersecting the first lumen near the distal end of the delivery device;

an embolization coil comprising a continuous wire extending between a distal end and a proximal end, the wire having a substantially uniform cross-section without any discontinuities between the distal and the proximal ends thereof, the embolization coil being disposed within the first lumen of the delivery device, the embolization coil configured to be deployed into the target tissue for effecting a treatment thereof;

a deployment device disposed within the first lumen of the delivery device, the deployment device being adapted to eject the embolization coil from the opening at the distal end of the delivery device and into the target tissue, and a means for separating the embolization coil into a plurality of separate embolization coils having different lengths upon deployment of at least a portion of the embolization coil into the target tissue, the means for separating comprising a cutting implement located proximate the distal end of the delivery device, the cutting implement being movably disposed within the second lumen of the shaft and operably connected to a proximal end of the delivery device, wherein the cutting implement comprises an electrosurgical wire that is configured to ensnare and sever the wire of the embolization coil into the plurality of separate embolization coils upon delivery of the at least a portion of the embolization coil into the target tissue, the electrosurgical wire being configured to sever the wire of the embolization coil at any location between the distal and proximal ends of thereof.

2. The delivery system according to claim 1, wherein the embolization coil includes a plurality of visualization indicators disposed at spaced apart locations.

3. The delivery system according to claim 2, wherein the visualization indicator can be visualized in vivo using one of ultrasound and fluoroscopy.

4. The delivery system according to claim 1, wherein the delivery device comprises a fluid delivery lumen in addition to the lumen in which the embolization coil is disposed.

5. The delivery system according to claim 1, wherein the delivery device comprises a fiber optic element extending to the distal end of the shaft, wherein the fiber optic element is disposed alongside the lumen in which the embolization coil is disposed.

6. The delivery system according to claim 1, wherein the delivery device comprises a hollow fiber optic element extending to the distal end of the shaft, wherein the embolization coil is disposed within the hollow fiber optic element.

7. The delivery system according to claim 1, wherein the embolization coil comprises an anchor configured to inhibit movement of embolization coil relative to the target tissue.

8. The delivery system according to claim 7, wherein the anchor comprises an expandable article.

9. The delivery system according to claim 7, wherein the anchor comprises a material that can be visualized in vivo using one of ultrasound and fluoroscopy.

10. The delivery system according to claim 7, wherein the anchor comprises a thrombogenic material.

11. A method of delivering one or more embolization coils to a lesion of a patient, the method comprising the steps of:
    providing an embolization coil delivery system according to claim 1;
    advancing an endoscope into the patient and positioning a distal end of the endoscope at a selected internal body location;
    advancing the shaft of the delivery device through a working channel of the endoscope so as to extend the distal end of the shaft beyond the distal end of the endoscope;
    using ultrasonic energy to guide the distal end of the shaft towards and into the lesion;
    deploying a first portion of the embolization coil from the distal end of the delivery device and into the lesion, and
    severing the first portion of the embolization coil from a second portion of the embolization coil, the second portion of the embolization coil remaining within the delivery device.

12. The method according to claim 11, further comprising the step of deploying a second portion of the embolization coil from the distal end of the delivery device and into the lesion.

* * * * *

UNITED STATES PATENT AND TRADEMARK OFFICE
CERTIFICATE OF CORRECTION

PATENT NO. : 8,328,841 B2
APPLICATION NO. : 12/154331
DATED : December 11, 2012
INVENTOR(S) : Michael J. Levy Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 368 days.

Signed and Sealed this
Twenty-eighth Day of October, 2014

Michelle K. Lee
*Deputy Director of the United States Patent and Trademark Office*